United States Patent
Lang et al.

(10) Patent No.: US 12,329,621 B2
(45) Date of Patent: Jun. 17, 2025

(54) TOPICALLY TREATED TISSUE PRODUCT

(71) Applicant: Kimberly-Clark Worldwide, Inc., Neenah, WI (US)

(72) Inventors: Frederick J. Lang, Neenah, WI (US); Kevin J. Vogt, Neenah, WI (US); Matthew R. Wilson, Oshkosh, WI (US); Christopher L. Satori, Hortonville, WI (US); Jessica C. Heiting, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 18/619,776

(22) Filed: Mar. 28, 2024

(65) Prior Publication Data

US 2024/0238134 A1    Jul. 18, 2024

Related U.S. Application Data

(62) Division of application No. 17/797,372, filed as application No. PCT/US2020/017008 on Feb. 6, 2020, now abandoned.

(51) Int. Cl.

| | | |
|---|---|---|
| *A61F 13/511* | (2006.01) | |
| *A61K 8/02* | (2006.01) | |
| *A61K 8/34* | (2006.01) | |
| *A61K 8/92* | (2006.01) | |
| *D21H 27/00* | (2006.01) | |
| *D21H 27/30* | (2006.01) | |

(52) U.S. Cl.
CPC ...... *A61F 13/51113* (2013.01); *A61K 8/0208* (2013.01); *A61K 8/34* (2013.01); *A61K 8/92* (2013.01); *D21H 27/002* (2013.01); *D21H 27/30* (2013.01)

(58) Field of Classification Search
CPC .......... A61K 8/0208; A61K 8/34; A61K 8/92; A61K 8/31; A61K 8/345; A61K 8/86; A61K 8/922; A61F 13/51113; A61F 19/00; A61F 2800/31; D21H 27/002; D21H 27/30; D21H 27/02; D21H 27/40; A47K 10/16
See application file for complete search history.

(56) References Cited

U.S. PATENT DOCUMENTS

| | | |
|---|---|---|
| 3,176,058 A | 3/1965 | Mittman |
| 3,337,388 A | 8/1967 | Wosaba, II |
| (Continued) | | |

FOREIGN PATENT DOCUMENTS

| | | |
|---|---|---|
| CN | 102555304 A | 7/2012 |
| EP | 0864014 B1 | 1/2002 |
| (Continued) | | |

*Primary Examiner* — Jose A Fortuna
(74) *Attorney, Agent, or Firm* — KIMBERLY-CLARK WORLDWIDE, INC.

(57) ABSTRACT

A low-cost, in-line process for treating a fibrous web with a lotion is provided. The process generally involves passing a web through a nip formed by a pair of opposed surfaces, where one of the surfaces has been treated with a lotion having a penetration hardness greater than 5.0 mm. As the web passes through the nip, the lotion is transferred from one of the opposed surfaces to the surface of the web. In certain instances, the web may have a textured surface and only a portion of the web's textured surface is treated with a lotion.

14 Claims, 5 Drawing Sheets

(56) References Cited

U.S. PATENT DOCUMENTS

| | | | |
|---|---|---|---|
| 3,692,622 | A | 9/1972 | Dunning |
| 4,166,758 | A | 9/1979 | Watanabe et al. |
| 4,191,609 | A | 3/1980 | Trokhan |
| 4,211,743 | A | 7/1980 | Nauta et al. |
| 4,528,239 | A | 7/1985 | Trokhan |
| 4,536,431 | A | 8/1985 | Wyckoff |
| 5,024,799 | A | 6/1991 | Harp et al. |
| 5,549,790 | A | 8/1996 | Van Phan |
| 5,624,676 | A | 4/1997 | Mackey et al. |
| 5,643,588 | A | 7/1997 | Roe et al. |
| 5,665,426 | A | 9/1997 | Krzysik et al. |
| 5,720,966 | A | 2/1998 | Ostendorf |
| 5,830,487 | A | 11/1998 | Klofta et al. |
| 5,840,403 | A | 11/1998 | Trokhan et al. |
| 5,869,075 | A | 2/1999 | Krzysik |
| 5,871,607 | A | 2/1999 | Hamilton et al. |
| 6,030,690 | A | 2/2000 | McNeil et al. |
| 6,099,940 | A | 8/2000 | Hamilton et al. |
| 6,106,928 | A | 8/2000 | Laurent et al. |
| 6,113,740 | A | 9/2000 | Oriaran et al. |
| 6,117,525 | A | 9/2000 | Trokhan et al. |
| 6,179,961 | B1 | 1/2001 | Ficke et al. |
| 6,217,707 | B1 | 4/2001 | Garvey et al. |
| 6,238,682 | B1 | 5/2001 | Klofta et al. |
| 6,277,226 | B1 | 8/2001 | Schulz |
| 6,277,467 | B1 | 8/2001 | Dwiggins et al. |
| 6,398,909 | B1 | 6/2002 | Klerelid |
| 6,420,013 | B1 | 7/2002 | Vinson et al. |
| 6,470,945 | B1 | 10/2002 | Biagiotti |
| 6,547,928 | B2 | 4/2003 | Barnholtz et al. |
| 6,701,637 | B2 | 3/2004 | Lindsay et al. |
| 6,716,309 | B2 | 4/2004 | Chuang et al. |
| 6,960,349 | B2 | 11/2005 | Shantz et al. |
| 6,984,290 | B2 | 1/2006 | Runge et al. |
| 7,351,308 | B2 | 4/2008 | Urlaub et al. |
| 7,396,593 | B2 | 7/2008 | Liu et al. |
| 7,470,345 | B2 | 12/2008 | Troxell et al. |
| 7,988,823 | B2 | 8/2011 | Burazin et al. |
| 8,260,592 | B2 | 9/2012 | Schmitt et al. |
| 8,455,077 | B2 | 6/2013 | Vinson et al. |
| 8,557,269 | B2 | 10/2013 | Kleinwaechter et al. |
| 9,243,368 | B2 | 1/2016 | Mellin et al. |
| 10,669,674 | B2 | 6/2020 | Olson |
| 10,689,810 | B2 | 6/2020 | Baum et al. |
| 11,466,409 | B2 * | 10/2022 | Tirimacco ............... D21H 25/14 |
| 11,732,406 | B2 * | 8/2023 | Suer ........................ D06N 7/00 |
| | | | 428/156 |
| 2003/0010228 | A1 | 1/2003 | Lofink |
| 2003/0026950 | A1 | 2/2003 | Kershaw et al. |
| 2003/0111169 | A1 | 6/2003 | Baggot et al. |
| 2004/0007338 | A1 | 1/2004 | Neveu et al. |
| 2004/0020614 | A1 | 2/2004 | Lindsay et al. |
| 2004/0055721 | A1 | 3/2004 | Hilbig et al. |
| 2005/0098281 | A1 | 5/2005 | Schulz et al. |
| 2005/0238700 | A1 | 10/2005 | Kleinwaechter et al. |
| 2005/0258576 | A1 | 11/2005 | Forry et al. |
| 2006/0137840 | A1 | 6/2006 | Burazin et al. |
| 2006/0278357 | A1 | 12/2006 | Suzuki et al. |
| 2006/0286885 | A1 | 12/2006 | Schuh et al. |
| 2007/0071797 | A1 | 3/2007 | Hernandez-Munoa et al. |
| 2007/0137808 | A1 | 6/2007 | Lostocco et al. |
| 2008/0318004 | A1 | 12/2008 | Ruhe et al. |
| 2009/0056860 | A1 | 3/2009 | Evans, Jr et al. |
| 2009/0199986 | A1 | 8/2009 | Biagiotti |
| 2009/0226670 | A1 | 9/2009 | Schütz |
| 2010/0233440 | A1 | 9/2010 | Tsai |
| 2010/0297286 | A1 | 11/2010 | Boatman et al. |
| 2010/0297402 | A1 | 11/2010 | Boatman et al. |
| 2010/0326613 | A1 | 12/2010 | Denis et al. |
| 2013/0004602 | A1 | 1/2013 | Mootz et al. |
| 2013/0068868 | A1 | 3/2013 | Hermans et al. |
| 2013/0337243 | A1 | 12/2013 | Ishikawa et al. |
| 2015/0225903 | A1 | 8/2015 | Jeannot et al. |
| 2018/0142422 | A1 | 5/2018 | Baum et al. |
| 2018/0213981 | A1 | 8/2018 | Vogt et al. |
| 2018/0216298 | A1 | 8/2018 | Vogt et al. |
| 2019/0078262 | A1 * | 3/2019 | Vogt ...................... D21H 17/07 |
| 2019/0133385 | A1 | 5/2019 | Vogt et al. |
| 2023/0070834 | A1 * | 3/2023 | Lang .................... D21H 27/002 |
| 2024/0238134 | A1 * | 7/2024 | Lang .................... D21H 27/002 |

FOREIGN PATENT DOCUMENTS

| | | | | |
|---|---|---|---|---|
| EP | 3979974 B1 * | 9/2024 | ......... | A61F 13/8405 |
| JP | H11323787 A | 11/1999 | | |
| NZ | 588750 A | 5/2012 | | |
| WO | 1997048854 A1 | 12/1997 | | |
| WO | 2010009769 A1 | 1/2010 | | |
| WO | 2011080941 A1 | 7/2011 | | |
| WO | 2014004939 A1 | 1/2014 | | |
| WO | 2014181389 A1 | 11/2014 | | |
| WO | WO-2017165358 A1 * | 9/2017 | ............ | A47K 10/16 |
| WO | WO-2017196519 A1 * | 11/2017 | ............ | A47K 10/16 |
| WO | 2020174709 A1 | 9/2020 | | |
| WO | WO-2023149869 A1 * | 8/2023 | | |

\* cited by examiner

TOPICALLY TREATED TISSUE PRODUCT

BACKGROUND

Absorbent tissue products such as facial tissue and bath tissue have been used to absorb body fluids and leave the skin dry. Absorbent tissue, in addition to absorbing fluids, however, also abrade the skin during use and frequently do not leave the skin completely dry and free of the body fluid the tissue is trying to absorb. During frequent nose-blowing or perianal wiping, the skin can become so abraded as to appear red and be sore to the touch. To reduce skin abrasion, tissue additive formulations can be applied to the tissue such that, in use, the additive formulation either provides lubricity causing the tissue to glide across the surface of the skin or leaves the tissue and is deposited on the skin. To date, these formulations have been liquids or lipid (lipophilic materials) based semi-solids or lipid-based solids at room temperature. The liquid or lipid-based semi-solid type of formulations require a high amount of formulation added to the tissue to deliver the benefit of reduced skin irritation and redness because these formulations absorb into a tissue, leaving less on the surface to provide the benefit. The lipid based solid formulations can be heated (slightly above the melting point of the formulation) and applied to the surface of a tissue or towel thereafter re-solidifying the formulation on the surface (s) of the tissue where the formulation is readily available for transfer to the user's skin to protect the skin from or prevent further irritation and redness in an efficient cost-effective manner.

While the foregoing formulations have been successfully employed in the manufacture of tissue products, they leave much to be desired. For example, their application often requires complex and expensive off-line processes such as rotogravure printing, flexographic printing or spraying. These methods are not only complex and expensive, they generally treat more of the tissue surface than is necessary to achieve the desired user benefit. Accordingly, there remains a need in the art for a low cost, in-line process for selectively treating a tissue product with a lotion.

SUMMARY

A low-cost, in-line process for treating a fibrous web with a lotion has now been discovered. The inventive process is particularly useful in treating fibrous webs, particularly textured tissue webs, with a lotion. In certain instances, the method may be used to selectively dispose lotion on only a portion of the structure's surface. For example, in certain embodiments, the present invention provides a process for selectively treating the surface of a textured fibrous structure, such as a textured structure having a first side with first and second surfaces lying in different surface planes, by passing the structure through a nip formed by a rotating roll having lotion disposed thereon. As the structure passes through the nip a portion of the lotion is transferred from the roll to the upper most surface of the structure. In this manner, only a portion of the structure's first side is treated with a lotion.

Accordingly, in one embodiment the present invention provides a method of applying a solid lotion to a fibrous web comprising the steps of providing solid lotion compositions having a penetration hardness greater than about 5.0 mm, such as from about 5.0 to about 30 mm, measured pursuant to the Hardness Method set forth below, and applying the lotion to a transfer surface to form a film on the transfer surface. Next, at least one outwardly-facing surface of a fibrous web is contacted with the transfer surface resulting in a transfer of the lotion to the surface of the fibrous web. In certain instances, the amount of lotion transfer to the web may be less than about 3.0 grams per square meter (gsm) of fibrous web and more preferably less than about 2.0 gsm and still more preferably less than about 1.0 gsm, such as from about 0.10 to about 3.0 gsm, such as from about 0.5 to about 2.0 gsm.

In other embodiments the present invention provides a method for applying a lotion on a textured fibrous structure after the textured fibrous structure has been formed and substantially dried. The method comprises providing a nip between a rotating roll having a substantially smooth surface and an opposed surface, applying a lotion to the rotating roll and conveying a textured tissue web through the nip. As the textured web passes through the nip the lotion is transferred from the rotating roll to the textured tissue web.

In another embodiments the invention provides a method of manufacturing a treated tissue web where a lotion is topically applied to the web without a significant reduction in the overall surface topography of the structure. Accordingly, the present method may be used as a means of topically applying a lotion to a structure while maintaining the texture of the structure. For example, the methods of the present invention may be useful in producing a textured tissue web comprising a plurality of ridges having upper surfaces lying in a first surface plane and a plurality of valleys lying in a second surface plane and a lotion selectively disposed on the upper surfaces of the plurality of ridges.

In yet another embodiment the present invention provides a calender coated tissue product comprising at least one calendered tissue web having an upper surface and a lotion disposed on the upper surface. Preferably the lotion is present on the upper surface in an amount less than about 3.0 grams per square meter (gsm) of fibrous web and more preferably less than about 2.0 gsm and still more preferably less than about 1.0 gsm, such as from about 0.10 to about 3.0 gsm, such as from about 0.5 to about 2.0 gsm.

In still other embodiments the present invention provides a treated fibrous structure having a first side comprising first and second surfaces lying in first and second surface planes where there is a z-directional height difference between the first and the second surface planes. The first side further comprises a lotion selectively disposed on the first surface. Preferably the second surface is substantially free from the lotion. Preferably the lotion composition is applied indirectly to the fibrous structure and is a solid having a penetration hardness greater than about 5 mm, such as from about 5.0 to about 30 mm, more particularly from about 10 to about 25 mm, and still more particularly from about 12 to about 20 mm. As referred to herein, the penetration hardness of a lotion is measured pursuant to the Hardness Method set forth below.

In still other embodiments the present invention provides a through-air dried tissue product comprising at least one through-air dried tissue web having a textured first side having a first surface lying in a first surface plane and a second surface lying in a second surface plane, wherein the first surface comprises from about 70 to about 95 percent of the surface area of the first side of the web and comprises a lotion selectively disposed thereon.

In yet other embodiments the present invention provides a treated tissue product comprising a lotion selectively applied to only a portion of the product surface at relatively low add-on levels. The lotion may be selectively applied such than 100 percent or less of the surface area of the product is treated, such as from about 70 to about 90 percent and more preferably from about 10 to about 20 percent. Further, the add-on of lotion (on a solids basis) relative to the dry fiber weight of the product can be less than about 3.0 grams per square meter (gsm) of web, such as less than about 2.0 gsm, such as less than about 1.0 gsm.

DESCRIPTIONS OF THE DRAWINGS

DEFINITIONS

Figure 1:
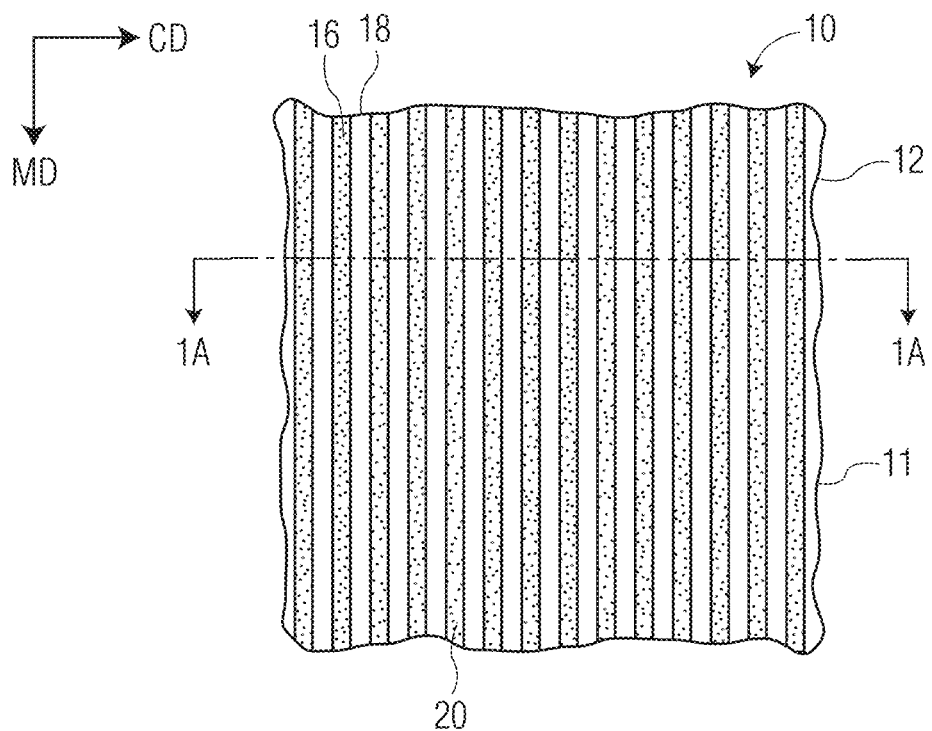
FIG. 1 is a plan view of a fibrous structure according to one embodiment of the present invention with FIG. 1A representing a cross-sectional view of the structure through line 1A-1A.

As used herein the term "fibrous structure" refers to a structure comprising a plurality of elongated particulate having a length to diameter ratio greater than about 10 such as, for example, papermaking fibers and more particularly pulp fibers, including both wood and non-wood pulp fibers, and synthetic staple fibers. A non-limiting example of a fibrous structure is a tissue web comprising pulp fibers.

As used herein the term "basesheet" refers to a fibrous structure provided in sheet form that has been formed by any one of the papermaking processes described herein but has not been subjected to further processing to convert the sheet into a finished product, such as subtractive texturing, embossing, calendering, perforating, plying, folding, or rolling into individual rolled products.

As used herein the term "tissue web" refers to a fibrous structure provided in sheet form and being suitable for forming a tissue product.

As used herein the term "tissue product" refers to products made from tissue webs and includes, bath tissues, facial tissues, paper towels, industrial wipers, foodservice wipers, napkins, medical pads, and other similar products. Tissue products may comprise one, two, three or more plies.

As used herein the term "ply" refers to a discrete tissue web used to form a tissue product. Individual plies may be arranged in juxtaposition to each other.

As used herein the term "layer" refers to a plurality of strata of fibers, chemical treatments, or the like, within a ply.

As used herein, the term "papermaking fabric" means any woven fabric used for making a tissue sheet, either by a wet-laid process or an air-laid process. Specific papermaking fabrics within the scope of this invention include wet-laid through-air drying fabrics and air-laid forming fabrics.

As used herein, the term "textured" generally refers the three-dimensional topography of a first or a second side of a fibrous structure. Generally, a textured structure will have a first side with first and second surfaces lying in first and second surface planes where there is some non-zero z-direction height difference between the first and second surface planes. For example, in one-embodiment, a textured tissue web may comprise a plurality of elevated elements having an upper surface lying in a first surface plane separated from one another by land areas lying in a second surface plane.

As used herein, the term "surface plane" generally refers to the plane formed by the upper most surface of an element disposed on one side of a fibrous structure. A surface plane may be determined by well-known imaging techniques such as, for example, using a VHX-1000 Digital Microscope (manufactured by Keyence Corporation of Osaka, Japan) equipped with VHX-H3M application software or other suitable image analysis software.

As used herein, the term "design element" means a decorative figure, icon or shape such as a line element, a flower, heart, puppy, logo, trademark, word(s) and the like. A design element may comprise a portion of the fibrous structure surface that lies out of plane with the land or background areas.

As used herein the term "line element" refers to an element, such as a design element, in the shape of a line, which may be continuous, discrete, interrupted, and/or a partial line with respect to a fibrous structure on which it is present. The line element may be of any suitable shape such as straight, bent, kinked, curled, curvilinear, serpentine, sinusoidal, and mixtures thereof, that may form regular or irregular periodic or non-periodic lattice work or structures wherein the line element exhibits a length along its path of at least 10 mm. In one example, the line element may comprise a plurality of discrete elements, such as dots and/or dashes for example, that are oriented together to form a line element.

As used herein the term "continuous element" refers to an element, such as a design element, disposed on a fibrous structure that extends without interruption throughout one dimension of the fibrous structure.

As used herein the term "discrete element" refers to an element, such as a design element, disposed on a fibrous structure that does not extend continuously in any dimension of the fibrous structure.

As used herein the term "basis weight" generally refers to the bone-dry weight per unit area of a tissue and is generally expressed as grams per square meter (gsm). Basis weight is measured using TAPPI test method T-220. While basis weight may be varied, tissue products prepared according to the present invention generally have a basis weight greater than about 10 gsm, such as from about 10 to about 80 gsm and more preferably from about 30 to about 60 gsm.

As used herein the term "caliper" is the representative thickness of a single sheet (caliper of tissue products comprising two or more plies is the thickness of a single sheet of tissue product comprising all plies) measured in accordance with TAPPI test method T402 using an EMVECO 200-A Microgage automated micrometer (EMVECO, Inc., Newberg, OR). The micrometer has an anvil diameter of 2.22 inches (56.4 mm) and an anvil pressure of 132 grams per square inch (per 6.45 square centimeters) (2.0 kPa). The caliper of a tissue product may vary depending on a variety of manufacturing processes and the number of plies in the product, however, tissue products prepared according to the present invention generally have a caliper greater than about 100 µm, more preferably greater than about 200 µm and still more preferably greater than about 300 µm, such as from about 100 to about 1,500 µm and more preferably from about 300 to about 1,200 µm.

As used herein the term "sheet bulk" refers to the quotient of the caliper (generally having units of µm) divided by the bone-dry basis weight (generally having units of gsm). The resulting sheet bulk is expressed in cubic centimeters per gram (cc/g). While sheet bulk may vary depending on any one of a number of factors, tissue products prepared according to the present invention may have a sheet bulk greater than about 5 cc/g, more preferably greater than about 8 cc/g and still more preferably greater than about 10 cc/g, such as from about 5 to about 20 cc/g.

As used herein, the terms "geometric mean tensile" and "GMT" refer to the square root of the product of the machine direction tensile strength and the cross-machine direction tensile strength of the tissue product. While the GMT may vary, tissue products prepared according to the present invention may have a GMT greater than about 500 g/3", more preferably greater than about 700 g/3" and still more preferably greater than about 1,000 g/3".

DESCRIPTION

The present invention provides a variety of novel lotion treated fibrous structures and methods of producing the same. For example, the present invention provides tissue products, particularly products having three-dimensional surface topography, where a lotion is selectively applied to only a portion of the tissue surface. In other instances, the tissue products may be treated with two different lotions such as a first lotion disposed in a first cross-machine direction zone and a second lotion disposed in a second cross-machine direction zone. Preferably the first and second lotions differ in at least one regard, such as the first lotion being hydrophilic and the second lotion being hydrophobic.

While any fibrous structure may be treated with a lotion according to the present invention, in certain instances it may be preferable to treat a fibrous structure having a three-dimensional topography with portions of the structure upper surface lying in first and second surface planes. In certain preferred embodiments the first surface plane lies above the second surface plane and forms the upper most structure surface and is selectively treated with lotion. The second surface, which lies below the first surface, is generally free from lotion. In this manner, the surface of the structure may be selectively treated with lotion such that the surface first brought into contact with the user's skin in-use is selectively treated with lotion. In this manner, the amount of lotion added to the tissue may be reduced without negatively affecting user's perception of softness and comfort. Further, by reducing the amount of lotion and selectively applying it to only a portion of the structure, other important properties such as absorbency, strength and bulk may be preserved.

In certain embodiments the textured surface may comprise a first side having peaks or ridges lying in a first surface plane and valleys lying in a second surface plane below the first surface plane. In other embodiments the first side may comprise a first surface plane and a design element lying in a second surface plane below the first surface plane where the design element provides the fibrous structure with a visually discernable design which users may find aesthetically pleasing. Regardless of the shape and arrangement of elements the structures of the present invention generally have a first side having at least two different surface planes where the upper most surface is preferentially treated with a lotion.

Textured fibrous structures useful in the present invention may be created using any number of well-known techniques, such as wet molding or embossing. In certain preferred embodiments, texture is imparted to the fibrous structure during the manufacturing process such as by wet texturing, molding using a drying fabric or by embossing. Generally, the texture is not the result of printing.

Accordingly, in one embodiment, the fibrous structure is a wet-laid tissue web having a textured surface formed during the manufacturing process by molding the web using an endless belt having a corresponding textured surface. For example, the wet-laid tissue web may be manufactured using an endless belt which comprises a continuous three-dimensional element (also referred to herein as a continuous line element) and a reinforcing structure (also referred to herein as a carrier structure or fabric). The reinforcing structure comprises a pair of opposed major surfaces—a web contacting surface from which the continuous line elements extend and a machine contacting surface. Machinery employed in a typical papermaking operation is well known in the art and may include, for example, vacuum pickup shoes, rollers, and drying cylinders. In one embodiment the belt comprises a through-air drying fabric useful for transporting an embryonic tissue web across drying cylinders during the tissue manufacturing process. In such embodiments the web contacting surface supports the embryonic tissue web, while the opposite surface, the machine contacting surface, contacts the through-air dryer.

In certain embodiments a plurality of continuous line elements may be disposed on the web-contacting surface for cooperating with, and structuring of, the wet fibrous web during manufacturing. In a particularly preferred embodiment the web contacting surface comprises a plurality of spaced apart three-dimensional elements distributed across the web-contacting surface of the carrier structure and together constituting from at least about 15 percent of the web-contacting surface, such as from about 15 to about 35 percent, more preferably from about 18 to about 30 percent, and still more preferably from about 20 to about 25 percent of the web-contacting surface.

Figure 1A:
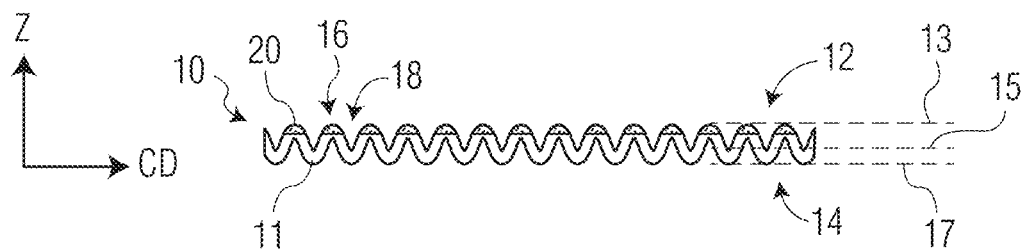

Now with reference to FIGS. 1 and 1A, one embodiment of a fibrous structure 10 prepared according to the present invention is illustrated. The fibrous structure 10 has two principle dimensions—a machine direction ("MD"), which is the direction substantially parallel to the principal direction of travel of the tissue web during manufacture and a cross-machine direction ("CD"), which is generally orthogonal to the machine direction. The fibrous structure generally has a textured first side 12 comprising a plurality of continuous elevated line elements 16, also referred to herein as ridges, and a plurality of valleys 18, also referred to herein as land areas, there-between.

The line elements 16 lie in a first surface plane 13 and the valleys lie in a second surface plane 15 and together form the surface of the first side 12. Opposite the first side 12 is the second side 14, lying in a bottom surface plane 17. While the instant fibrous structure is illustrated as having alternating ridges and valleys which define both the first and second sides and provide both with a textured surface, the invention is not so limited. For example, in an alternative embodiment the fibrous structure may comprise only one textured side. Moreover, while the illustrated line elements 16 and valleys 18 are both continuous the invention is not so limited, as will be discussed in further detail below.

With continued reference to FIGS. 1 and 1A the fibrous structure 10 comprises a lotion 20 selectively deposited on the ridges 16. In this manner the lotion 20 lies in the first surface plane 13 and is registered with the upper-most surface of the fibrous structure 10 such that it is the first surface to contact a user's skin in-use.

Figure 2:
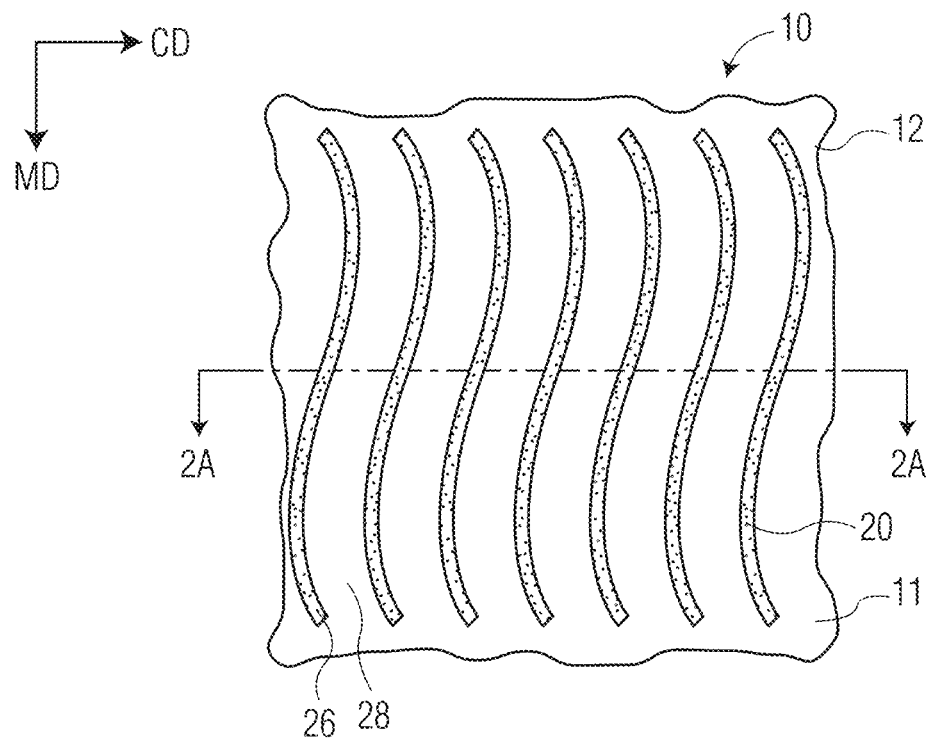
FIG. 2 is a plan view of a fibrous structure according to another embodiment of the present invention with FIG. 2A representing a cross-sectional view of the structure through line 2A-2A.
Figure 2A:
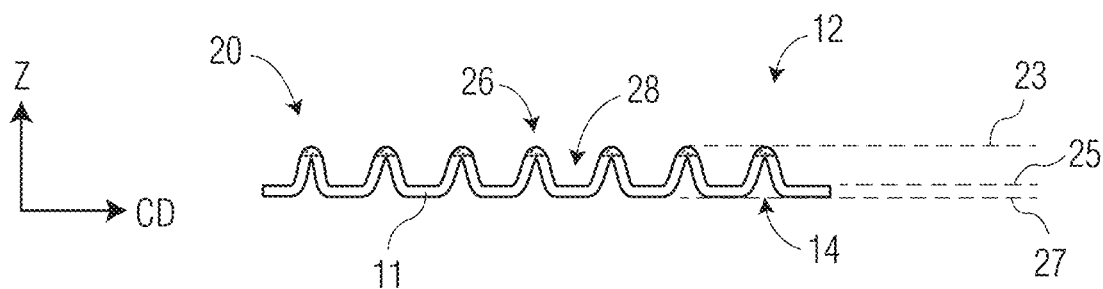

Turning now to FIGS. 2 and 2A, another embodiment of a fibrous structure 10 prepared according to the present invention is illustrated. The fibrous structure 10 comprises a plurality of discrete design elements 26 that form a portion of the first side 12 of the structure 10. The design elements 26 have an upper surface lying in a first surface plane 23. The design elements 26 are separated from one another by land areas 28, which have an upper surface lying in a second surface plane 25. The first surface plane 23 lies above the second surface plane 25 and together the discrete design elements 26 and the land areas 28 form the first side 12 of the structure. Opposite the first side 12 is a second side 14 that forms the bottom of the structure 10 and lies in a bottom surface plane 27.

A lotion 20 is selectively disposed on, in registration with, the discrete design elements 26. As such, the lotion 20 is selectively disposed on the upper most surface of the structure 10, while the land areas 28 are substantially free from lotion.

Figure 3:
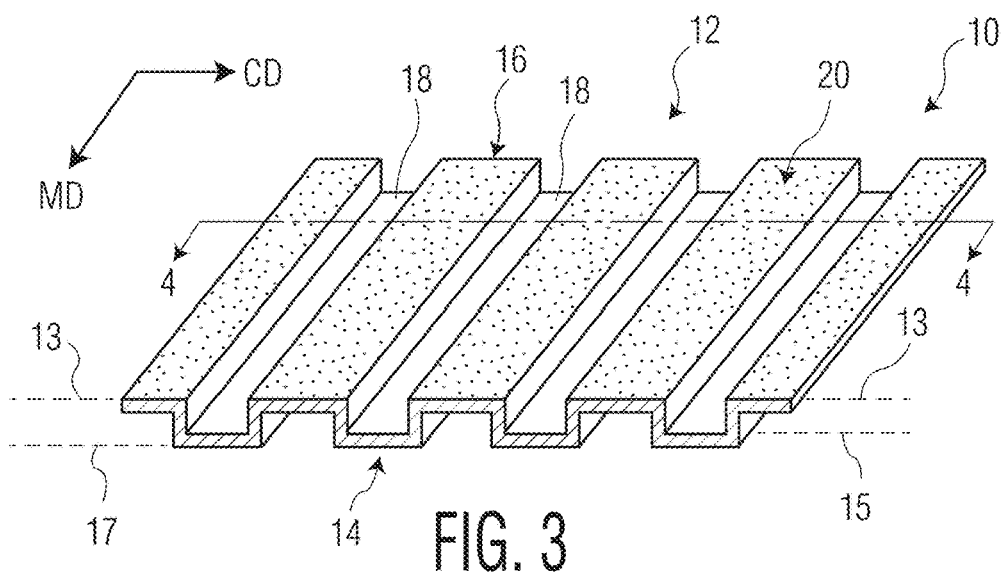
FIG. 3 is a perspective view of a lotion treated fibrous structure according to one embodiment of the present invention.
Figure 4:
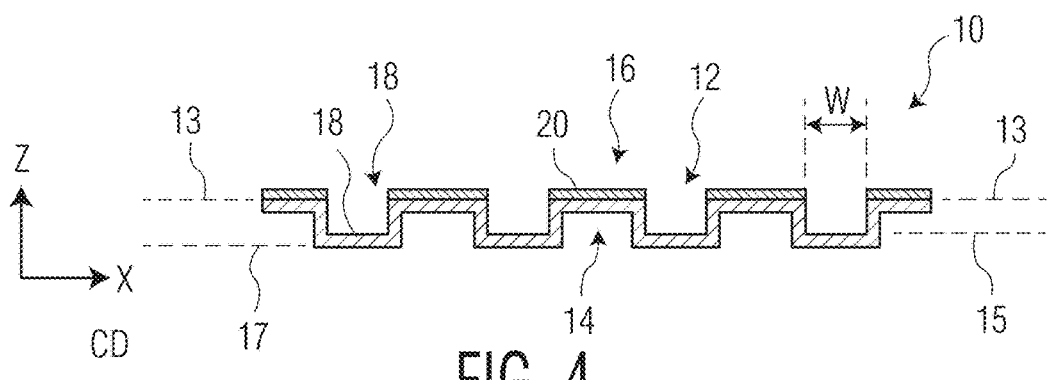
FIG. 4 is a cross-sectional view of the structure through line 4-4.

With reference now to FIG. 3, another embodiment of a fibrous structure 10 according to the present invention is provided. The first side 12 comprises continuous line elements 16, which are similarly sized and have generally straight, parallel spaced apart sidewalls that provide the continuous elements 16 with a width, and a height. The width and the height may be varied depending on the desired physical properties of the fibrous structure, such as sheet bulk and cross-machine direction stretch. In certain embodiments the height of the sidewalls is such that the resulting tissue structure has a caliper greater than about 300 μm, such as from about 300 to about 1,200 μm. The height is generally measured as the distance between the first surface plane 13 and the bottom surface plane 17.

The spacing and arrangement of the continuous line elements may vary depending on the desired tissue product properties and appearance. In one embodiment a plurality of line elements extend continuously throughout one dimension of the fibrous structure and each element in the plurality is spaced apart from the adjacent element. Thus, the elements may be spaced apart across the entire cross-machine direction of the fibrous structure or may run diagonally relative to the machine and cross-machine directions. Of course, the directions of the line elements alignments (machine direction, cross-machine direction, or diagonal) discussed above refer to the principal alignment of the elements. Within each alignment, the elements may have segments aligned at other directions, but aggregate to yield the particular alignment of the entire elements.

In addition to varying the spacing and arrangement of the elements, the shape of the element may also be varied. For example, in one embodiment, the elements are substantially sinusoidal and are arranged substantially parallel to one another such that none of the elements intersect one-another. As such the adjacent sidewalls of individual elements are equally spaced apart from one another. In such embodiments, the spacing of elements may be from about 1.0 to about 20 mm, and more preferably from about 2.0 to about 5.0 mm apart. The foregoing spacing may be optimized to maximum caliper of the fibrous structure, or provide a fibrous structure having a three-dimensional surface topography, yet relatively uniform density. Further, while in certain embodiments the elements are continuous the invention is not so limited. In other embodiments the elements may be discrete.

Further, while the elements are illustrated as having a square horizontal and lateral (relative to the upper surface plane) cross-sectional shape the invention is not so limited, and the elements may have any number of different horizontal and lateral cross-sectional shapes. A particularly preferred element is a line element having substantially planar sidewalls which are generally perpendicular to the upper surface plane. Further, while the uppermost surface of the element 16 is illustrated as being planar and defining a first surface plane 13, the invention is not so limited. For example, the element's upper surface may be non-planar, such as having further depressions in the form of lines or dots disposed thereon. Where the element's upper surface is non-planar the design element plane is generally defined by a line drawn tangent to the upper most point of the design element and parallel to the x-axis of the fibrous structure.

The individual elements, also referred to herein as design elements, may be arranged in any number of different manners to create a decorative pattern. In one particular embodiment design elements are spaced and arranged in a non-random pattern so as to create a wave-like design. Landing areas may be interspaced between adjacent individual design elements so as to provide a visually distinctive interruption to the decorative pattern formed by the individual spaced apart design elements. In this manner, despite being discrete elements, the design elements are spaced apart so as to form a visually distinctive curvilinear decorative element that extends substantially in the machine direction. In this manner, taken as a whole, the discrete elements may form a decorative pattern, such as a wave-like pattern.

In other embodiments the design elements may be spaced and arranged so as to form a decorative figure, icon or shape such as a flower, heart, puppy, logo, trademark, word(s) and the like. Generally, the design elements are spaced about the fibrous structure and can be equally spaced or may be varied such that the density and the spacing distance may be varied amongst the design elements. For example, the density of the design elements can be varied to provide a relatively large or relatively small number of design elements on the web. In a particularly preferred embodiment the design element density, measured as the percentage of one surface of the fibrous structure covered by a design element, is from about 5 to about 35 percent and more preferably from about 10 to about 30 percent. Similarly, the spacing of the design elements can also be varied, for example, the design elements can be arranged in spaced apart rows. In addition, the distance between spaced apart rows and/or between the design elements within a single row can also be varied.

Fibrous structures having textured surfaces which may be imparted with a design element of the present invention may be formed using any one of several well-known manufacturing processes. For example, in certain embodiments, fibrous structures may be produced by a through-air drying (TAD) manufacturing process, an advanced tissue molding system (ATMOS) manufacturing process, a structured tissue technology (STT) manufacturing process, or belt creped. In particularly preferred embodiments the fibrous structure is manufactured by a creped through-air dried (CTAD) process or uncreped through-air dried (UCTAD) process.

In one embodiment, tissue webs useful in the present invention are formed by the UCTAD process of: (a) depositing an aqueous suspension of papermaking fibers (furnish) onto an endless forming fabric to form a wet web; (b) dewatering or drying the web; (c) transferring the web to a transfer fabric; (d) transferring the web to a TAD fabric of the present invention having a pattern thereon; (e) deflecting the web wherein the web is macroscopically rearranged to substantially conform the web to the textured background pattern of the TAD fabric; and (f) through-air drying the web. In the foregoing process the web is not subject to creping but may be further processed as described below to impart a design pattern to the web.

After the basesheet is formed and dried it may be subjected to various converting process before final packaging. Prior to, or during this converting process, in accordance with the present invention, the basesheet is subjected to treatment with a lotion, which is preferably provided in solid form and transferred to a first surface of the basesheet by a transfer surface and more preferably a heated transfer surface.

In a particularly preferred embodiment, the transfer surface is a calender roll. In this manner a calendering-coating process may be used to selectively deposit a lotion on the surface of the web. This calendering-coating process may compress the web as it applies lotion to the upper most surface, effectively breaking some bonds formed between the fibers of the basesheet while selectively applying a lotion to its surface. The perceived softness of the basesheet is increased without significantly sacrificing tensile strength or any other characteristic thereof.

Figure 5:
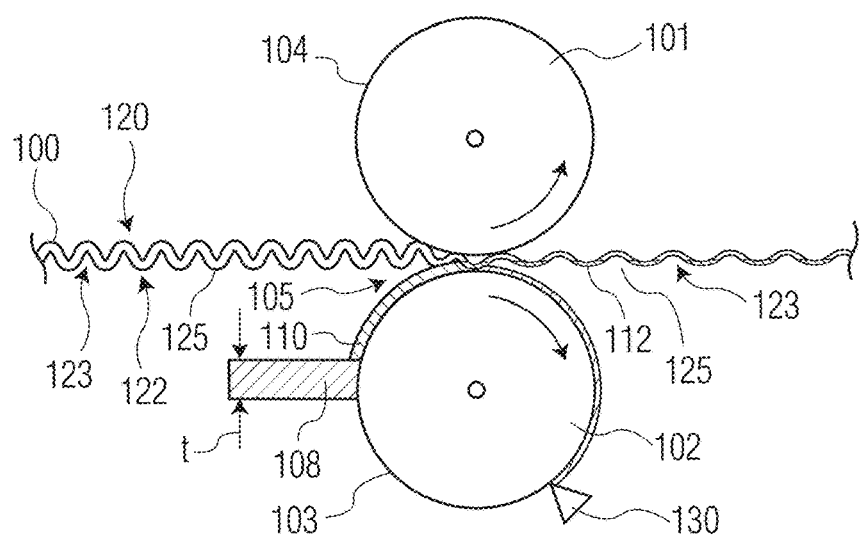
FIG. 5 is an illustration of an apparatus useful in forming the fibrous structures of the present invention.

Referring now to FIG. 5, one embodiment of a roll-gap apparatus useful for calendering-coating a fibrous structure according to the present invention is illustrated. In general, roll-gap calendering involves two calendering rolls 101 and 102 that compress the web 100, which may be textured in certain preferred embodiments. The surfaces 103, 104 of calendering rolls 101, 102 contacting the web 100 may comprise a variety of materials including, for example, metal such as steel or cast iron, or a polymeric material such as polyurethane, natural rubber (hard or soft), synthetic rubber, an elastomeric material, and the like. Furthermore, the roll surfaces can be smooth, roughened, or etched. In one embodiment, a first calendering roll 101 has a surface 104 comprising a polymer material and the second calendering roll 102 has a smooth metal surface 103.

The calendering-coating of the fibrous structure is achieved through compression of the fibrous structure in a nip 105 between the first and second calendering rolls 101 and 102. The two calendering rolls 101 and 102 are arranged to provide nip load, commonly having units of pounds per linear inch (pli) ranging from about 20 to about 120 pli, such as from about 40 to about 100 pli. While the embodiment illustrated in FIG. 5 relies upon a constant gap between the calendering rolls 101 and 102, the invention is not so limited, and the invention may be implemented using a calendering apparatus where the surfaces of the two rolls can be pressed together to form a pressure between the surfaces that compresses the base web at a higher pressure than the gap. However, depending on the load settings and the z-direction properties of the fibrous structure, it is possible to run the nipped mode at the same or even less pressure than the gap mode.

Both calendering rolls 101, 102 rotate so their respective surfaces 103, 104 move in the same direction as the web 100. In the embodiment illustrated in FIG. 5, the first calendering roll 101 is rotating counter-clockwise and the second calendering roll 102 is rotating clockwise. In certain instances, the fibrous structure moves from an unwind roll through a roll-gap calendering apparatus and is rewound onto a roll.

In a particularly preferred embodiment at least one of the calender rolls, particularly the roll to which the lotion is applied, is a roll having a metal surface and more preferably a heated steel roll with a substantially smooth surface. For example, with continued reference to FIG. 5, the lotion 108, which is provided in a solid state and has a penetration hardness greater than about 5.0 mm, such as from about 5.0 to about 30 mm (measured pursuant to the Hardness Method set forth below) is urged against the surface 103 of a second calendering roll 102, which preferably has a metal surface and is heated. The second calender roll may be heated such that its surface temperature is at least about 70° C., such as from about 70 to about 100° C. and more preferably from about 70 to about 90° C. The degree to which the second calender roll is heated may depend on the composition of the lotion and the desired lotion add-on.

Figure 6:
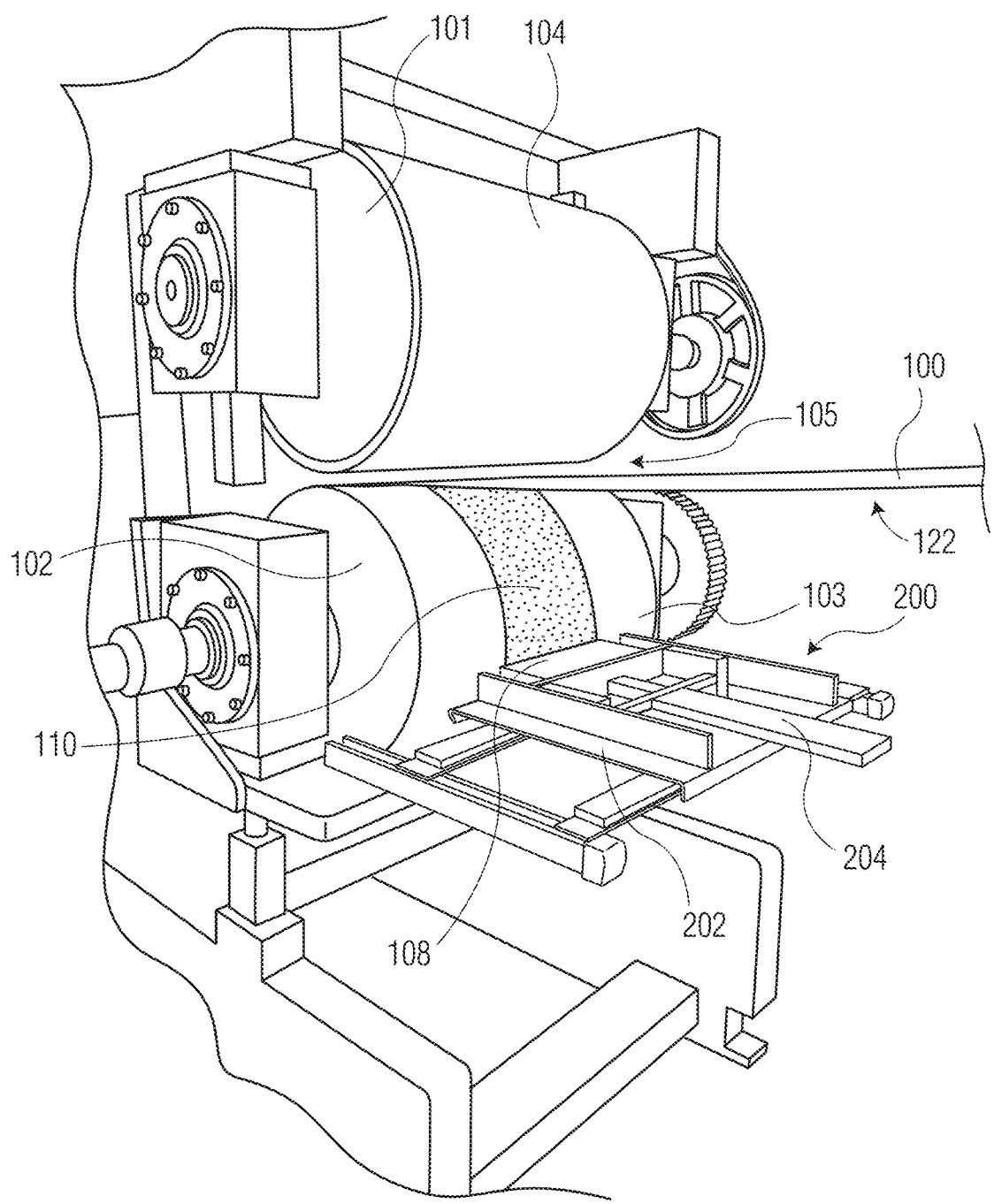
FIG. 6 is a perspective view of an apparatus useful in forming the fibrous structures of the present invention.

With reference now to FIG. 6, the calendering-coating apparatus may be provided with an applicator 200 for retaining a solid lotion 108, having a thickness (t), and urging the lotion against the surface 103 of a calender roll 102. In certain non-limiting instances, the lotion thickness (t) may range from about 1 to about 5 cm. Further, as discussed in more detail below, the lotion thickness (t) may be varied along with one or more process variables to control the amount of lotion added to the web. As the lotion 108 is urged against the calender surface 103 a coating of lotion 110 is applied. The lotion 110 may then be transferred to the surface of a web 100 as it passes through the nip 105.

The speed of the web 100 as it passes through the nip 105 may be varied to control the amount of lotion added to the web. In certain non-limiting instances, the web speed may range from about 15 to about 300 meters per minute, such as from about 50 to about 250 meters per minute.

The applicator 200 may comprise a holder 202 and an automatic indexing mechanism 204 for automatically advancing the solid lotion 108 towards the roll surface 103. The automatic indexing mechanism may include a pressure sensor for measuring and monitoring the pressure applied to the solid lotion as it is urged against the calender roll surface and a means for advancing the solid lotion towards the roll surface. In other embodiments the lotion applicator may comprise a holder and a mechanical means, such as a spring, to maintain the desired pressure against the solid lotion and urge it against the roll surface.

In certain preferred embodiments the automatic indexing mechanism 204 may advance the solid lotion 108 towards the roll surface 103 at a predetermined feed rate (FR) to achieve the desired add-on. For example, the feed rate may be varied from about 0.05 to about 0.2 mm per second to achieve an add-on from about 0.5 to about 6.0 grams per square meter (gsm) of web. In certain instances the desired add-on (having units of grams per square meter of web) may be achieved by controlling the thickness of the solid lotion (having units of mm or the like), the lotion feed rate (FR, having units of mm per second or the like), the penetration hardness of the lotion (measured as described herein and having units of mm) and the speed of the web (having units of meters per minute or the like) as it passes through the nip. For example, the desired lotion add-on may be related to lotion thickness, feed rate, penetration hardness and web speed by Equation 1, below.

$$\text{Lotion Add On} \propto \frac{\text{Thickness} \times \text{Feed Rate} \times \text{Penetration Hardness}}{\text{Web Speed}} \quad \text{Equation (1)}$$

For carrying out the calendering-coating process the solid lotion 108 is urged against the second calender roll 102 and a portion of the lotion is transferred to the roll surface 103. The lotion coated roll surface 110 is then brought into contact with the first side 122 of the web 100 in the calender nip 105. Within the nip, the lotion is transferred from the roll surface to the upper most surface of the first side 122 of the textured fibrous structure. After leaving the calender nip, the roll surface may be substantially free from lotion however, in certain instances it is possible that a lotion residue remains on the surface. Lotion residue on the leading rotating sector of the second calender roll 102 may be stripped from the outer surface thereof with the help of a doctor blade (shown in FIG. 5) or other stripping device.

After leaving the calender nip, the textured fibrous structure has been treated with the lotion, with the lotion oriented on the first side 122 and more particularly on the upper most surface of the first side 122. The lotion treated fibrous structure may be subjected to further processing, such as drying, to ensure that the lotion treatment retains its size, shape, configuration, or registration on the first side 122 of the structure as it was applied. It will be recognized by those skilled in the art that the particular configuration of the calender rolls 102, 104 and applicator 200 as shown in FIG. 6 is merely exemplary, and other configurations and set up of the apparatus may be used.

The total add-on amount of the lotion to the fibrous structure may be less than about 3.0 grams per square meter (gsm) of fibrous web and more preferably less than about 2.0 gsm and still more preferably less than about 1.0 gsm, such as from about 0.10 to about 3.0 gsm. In other instances, the lotion add-on may be expressed in terms as a percentage of the weight of the fibrous structure and may be less than about 5.0 percent, by weight of the web, such as from about 1.0 to about 5.0 percent and more preferably from about 2.0 to about 3.0 percent. The lotion add-on amount will depend upon the desired effect of the composition on the product attributes and the specific composition of the lotion.

Preferably the lotion is a solid at room temperature and is melted during the application process after which it re-solidifies to form a distribution, preferably a uniform distribution, of solid deposits on the upper most surface of a textured fibrous structure. Because the composition is a solid at room temperature and rapidly solidifies after deposition, it has less tendency to penetrate and migrate into the sheet. Compared to fibrous structures treated with liquid formulations, this leaves a greater percentage of the additive composition on the surface of the tissue where it can contact and transfer to the user's skin to provide enhanced skin health benefits. Furthermore, a lower add-on amount can be used to deliver the same benefit at a lower cost because of the efficient placement of the composition substantially at the surface of the product.

Solid lotions useful in the present invention may be provided with a range of different product forms. One of these is a so-called "stick" which is usually a bar of an apparently firm solid material held within an applicator and which retains its structural integrity and shape while being urged against a calender roll. When a portion of the stick is drawn across the surface of a calender roll a film of the stick composition is transferred to the roll surface. Although the stick has the appearance of a solid article capable of retaining its own shape for a period of time, the material usually has a structured liquid phase so that a film of the composition is readily transferred from the stick to roll surface upon contact.

Lotion compositions useful in the present invention may be provided as solids that are characterized by their retaining their shape without lateral support under the influence of the Earth's gravity, at temperatures up to at least 50° C. The hardness of the solid lotions can be measured in a needle penetration test. Pursuant to this test, as the solid lotions become softer, their needle penetration hardness values increase, with higher hardness values being indicative of a softer lotion composition. In one embodiment it is desirable that the lotion compositions have a penetration hardness greater than about 5.0 mm, such as from about 5.0 to about 30 mm, more particularly from about 7.0 to about 25 mm, more particularly from about 12 to about 22 mm, and still more particularly from about 16 to about 22 mm measured pursuant to the Hardness Method set forth below. Hardness values within these ranges are indicative of self-supporting solid lotions having a somewhat soft feel but are well suited for indirect application to a tissue web via a conventional calendering apparatus.

In particularly preferred embodiments lotions useful in the present invention are formulated as hydrophobic compositions. The hydrophobic lotions of the present invention preferably do not comprise added water, which could require an additional drying step. However, minor or trace quantities of water in the lotion that are picked as a result of, for example, ambient humidity can be tolerated without adverse effect. Typically, hydrophobic lotions useful in the present invention are provided as a solid stick having a penetration hardness ranging from about 5.0 to about 30 mm and contain about 3 percent or less water, preferably about 1 percent or less water, most preferably about 0.5 percent or less water.

In certain instances, the solid lotion composition may be hydrophobic and comprise one or more oils. The amount of oil in the composition can be from about 30 to about 90 weight percent, more specifically from about 40 to about 70 weight percent, and still more specifically from about 45 to about 60 weight percent. Suitable oils include, but are not limited to, the following classes of oils: petroleum or mineral oils, such as mineral oil and petrolatum; or animal oils, such as mink oil and lanolin oil.

Particularly preferred oils are mineral oils such as petroleum derivatives comprising a mixture of paraffinic and naphthenic (cyclic) hydrocarbons. These include both "light" and "heavy" mineral oils, which are differentiated on the basis of the average molecular weight of the hydrocarbons included. The mineral oils useful herein have the following properties: viscosity of from about 5 centistokes to about 70 centistokes at 40° C.; density between about 0.82 and about 0.89 g/cm$^3$ at 25° C.; flash point between about 138° C. and about 216° C.; and carbon chain length between about 14 and about 40 carbons.

In other instances, lotions useful in the present invention may comprise a wax. The amount of wax in the composition can be from about 10 to about 40 weight percent, more specifically from about 10 to about 30 weight percent, and still more specifically from about 15 to about 25 weight percent. Suitable waxes include, but are not limited to, the following classes: natural waxes, such as beeswax and carnauba wax; petroleum waxes, such as paraffin and ceresine wax; silicone waxes, such as alkyl methyl siloxanes; or synthetic waxes, such as synthetic beeswax and synthetic sperm wax.

In still other instances, lotions useful in the present invention may comprise one or more fatty alcohol, which may be present in amounts ranging from about 5 to about 40 weight percent, and more specifically from about 10 to about 30 weight percent. Suitable fatty alcohols include alcohols having a carbon chain length of $C_{14}$-$C_{30}$, including acetyl alcohol, stearyl alcohol, behenyl alcohol, and dodecyl alcohol.

In particularly preferred embodiments lotions useful in the present invention may be provided as a solid stick having a penetration hardness ranging from about 5.0 to about 30 mm and comprising from about 30 to about 90 weight percent oil, and from about 10 to about 40 weight percent wax, preferably also containing from about 5 to about 40 weight percent fatty alcohol.

In other embodiments lotions useful in the present invention may be provided as a solid stick having a penetration hardness ranging from about 5.0 to about 30 mm and comprising from about 20 to about 50 weight percent mineral oil and from about 10 to about 30 weight percent ceresin wax having a melting point from 64 to 67° C. and from about 10 to about 30 weight percent fatty alcohol selected from the group consisting of cetyl alcohol, stearyl alcohol, behenyl alcohol, and dodecyl alcohol.

In order to better enhance the benefits to a user, additional ingredients may optionally be included in a lotion useful in the present invention. Optional ingredients and their corresponding benefits include, without limitation, $C_{10}$ or greater fatty alcohols (lubricity, body, opacity), fatty esters (lubricity, feel modification), vitamins (topical medicinal benefits), dimethicone (skin protection), powders (lubricity, oil absorption, skin protection), preservatives and antioxidants (product integrity), ethoxylated fatty alcohols (wetability, process aids), fragrance (consumer appeal), lanolin derivatives (skin moisturization), colorants, optical brighteners, sunscreens, alpha hydroxy acids, natural herbal extracts, and the like. In a particularly preferred embodiment, the lotion comprises one or more oils selected from the group consisting of plant oils, such as aloe extract, sunflower oil and avocado oil, and silicone oils, such as dimethicone and alkyl methylsilicones.

While in certain instances lotions useful in the present invention may be provided in hydrophobic forms, the invention is not so limited. In other instances, the lotion may be hydrophilic and comprise water. Preferably hydrophilic lotions are provided as a solid stick having a penetration hardness ranging from about 5.0 to about 30 mm and comprise from 70 to 99.5 weight percent hydrophilic solvent. Suitable hydrophilic solvents include, but are not limited to, the following materials: water, propylene glycol, polyethylene glycol, methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol, hydrogenated starch hydrolysate, and silicone glycols.

Particularly preferred hydrophilic solvents are high molecular weight polyethylene glycols. As used herein "high molecular weight polyethylene glycols," generally refer to polyethylene glycols having an average molecular weight of 400 or greater, such as 600 or greater, such as 700 or greater. Particularly preferred are high molecular weight polyethylene glycols that are not liquid at room temperature, such as polyethylene glycols having an average molecular weight from about 700 to about 10,000, such as from about 700 to about 5,000, such as from about 700 to about 3,500. The solid hydrophilic lotion may comprise from 70 to 99.5 weight percent weight percent high molecular weight polyethylene glycol and have a penetration hardness ranging from about 5.0 to about 30 mm.

In other embodiments, the solid hydrophilic lotion may comprise propylene glycol, glycerin and a fatty alcohol. For example, the hydrophilic lotion may comprise from about 30 to about 95 weight percent propylene glycol, from about 30 to about 60 weight percent glycerin and from about 1 to about 10 weight percent of a fatty alcohol. Suitable fatty alcohols include, but are not limited to, alcohols having a carbon chain length of $C_{14}$-$C_{30}$, including cetyl alcohol, stearyl alcohol, arachidyl alcohol, and behenyl alcohol.

In certain instances, the hydrophilic lotion composition may comprise water, such as from about 10 to about 25 weight percent, more specifically from about 10 to about 20 weight percent, more specifically from about 12 to about 18 weight percent.

The application method of the present invention not only enables selective treatment of a structure's surface with a lotion, it also enables the application of two or more different lotions in a zoned manner across the cross-machine direction of the product. For example, in certain embodiments, a first and a second lotion, which differ from one another in at least one respect, may be disposed in a holder and urged against the surface of a calender roll and transferred to the surface of a web passing through a nip as described herein. The resulting treated web will have the first lotion disposed in a first cross-machine direction zone and the second lotion disposed in a second cross-machine direction zone. In other instances, a substantially similar lotion may be applied to the first and second zones, but the amount of lotion applied to a given zone may differ.

In certain preferred embodiments the present invention provides a treated tissue product having a machine direction and a cross-machine direction, a first side and an opposed second side, the tissue product comprising a first discrete cross-machine direction zone having a first lotion composition disposed thereon and a second discrete cross-machine direction zone having a second lotion composition disposed thereon, wherein the first and the second lotion compositions differ in at least one respect. In such embodiments, the term "discrete" generally refers to cross-machine direction zones that are separate and distinct from one another and do not overlap to any extent. In this manner, for example, a tissue product may comprise a hydrophobic lotion disposed in a first discrete cross-machine direction zone and a hydrophilic lotion disposed in a second discrete cross-machine direction zone. The first and second zones may be disposed immediately adjacent to one another or they may be spaced apart from one another with a third cross-machine direction zone disposed therebetween. In those instances where the first and second zones are separated from one another by a third zone, the third zone may be treated with a third lotion or may be untreated.

In those instances where the lotion treated tissue product comprises first and second cross-machine direction zones, the first zone may desirably have a cross-machine direction width dimension of from about 0.5 to about 12 cm, such as about 0.5 to about 10 cm, more specifically from about 1.0 to about 5.0 cm. The second zone may desirably have a width dimension equal to, greater than, or less than the width of the first zone, such as about 0.2 to about 12 cm, more specifically from about 0.2 to about 10 cm, and still more specifically from about 1.0 to about 5.0 cm. If present at all, a third zone, which is substantially free from lotion, may separate the first and second zones and have a width dimension of from about 0.02 to about 5 cm. It should be appreciated that there might be conditions such as cost, wiping task, and the like that would change the first, second and third zone size relationships. The length dimensions of the cross-machine direction zones may extend over the entire machine direction length of the tissue or only over part of the machine direction length of the tissue.

Tissue webs and products produced according to the present invention not only comprise a lotion that may be readily available for transfer to the user's skin to protect the skin from or prevent further irritation and redness, they may also have favorable physical properties, such as sufficient strength to withstand use without being stiff or rough. Accordingly, in one embodiment of the present invention a tissue product has a basis weight from about 10 to about 80 gsm, and more preferably from about 15 to about 60 gsm and a sheet bulk greater than about 5.0 cc/g, such as from about 5.0 to about 20 cc/g and more preferably greater than about 10 cc/g, such as from about 10 to about 20 cc/g.

In addition to having the foregoing basis weights and sheet bulks, tissue webs and products prepared according to the present invention may have a geometric mean tensile (GMT) greater than about 500 g/3", such as from about 500 to about 1,500 g/3", and more preferably from about 600 to about 1,000 g/3". At these tensile strengths the tissue webs and products have relatively low geometric mean modulus, expressed as GM Slope, so as to not overly stiffen the tissue product. Accordingly, in certain embodiments, tissue webs and products may have GM Slope less than about 20 kg, and more preferably less than about 15 kg and still more preferably less than about 10 kg.

In one particularly preferred embodiment the present invention provides a lotion rolled bath tissue product having a basis weight from about 20 to about 45 gsm, a GMT from about 500 to about 1,200 g/3", a GM Slope less than about 12 kg, such as from about 5.0 to about 12 kg, and a GM Stretch greater than about 5 percent, such as from about 5 to about 15 percent. The foregoing rolled bath tissue product preferably comprises at least one textured tissue web having a first side with first and second surfaces lying in first and second surface planes. The z-directional height difference between the first and second surface planes may be from about 100 to about 300 μm and more preferably from about 150 to about 250 μm.

The inventive single ply tissue webs may be plied together with other single ply webs prepared according to the present disclosure or with single ply webs of the prior art to form multi-ply tissue products using any ply attachment means known in the art, such as mechanical crimping or adhesive.

When two or more inventive tissue webs are joined together the resulting multi-ply tissue product may have a basis weight greater than about 40 gsm, such as from about 40 to about 80 gsm, and more preferably from about 50 to about 60 gsm. At these basis weights the tissue products generally have calipers greater than about 300 μm, such as from about 300 to about 1,200 μm, and more preferably from about 400 to about 1,000 μm. The tissue products further have sheet bulks greater than about 5.0 cc/g, such as from about 5.0 to about 20 cc/g and more preferably from about 10 to about 20 cc/g.

The inventive tissue products may also have relatively low modulus so as not to be overly stiff. For example, in certain embodiments the present invention provides lotion treated tissue products having a GMT greater than about 700 g/3", such as from about 700 to about 1,200 g/3", and geometric means slopes (GM Slopes) less than about 12.0 and more preferably less than about 10.0 kg, such as from about 4.0 to about 12.0 kg, such as from about 4.0 to about 10.0 kg, such as from about 4.0 to about 7.0 kg. At the foregoing strengths, inventive tissue products may have a Stiffness index less than about 10.0, such as from about 4.0 to about 10.0, such as from about 4.0 to about 8.0.

Test Methods

Penetration Hardness

The hardness and rigidity of a composition, such as a lotion useful in the present invention, which is a firm solid can be determined by penetrometry. If the composition is a softer solid, this will be observed as a substantial lack of any resistance to the penetrometer probe.

A suitable procedure for measuring penetration hardness utilizes Precision Scientific Model No. 73510 penetrometer equipped with a C521 needle (weight 2.5 grams) which has a cone angle at the point of the needle specified to be 9° 10'±15'. A 50 g weight is added to the plunger rod (47.5 g) for a combined testing load of approximately 100 g. Tests were conduct at approximately 20° C.

A sample of the composition with a flat upper surface is placed on the base of the penetrometer. The height of the mechanism head is adjusted so that the point of the penetrometer needle is brought exactly into contact with the surface of the sample. With the instrument zeroed, the test rod is released allowing the needle to descend into the sample. The release lever is depressed (held open) for a period of 5 seconds after which it is then released (closed). The depth gauge rod is then pressed down gently as far as it will go and the penetration depth is read from the gauge. Desirably the test is carried out at five (5) points on each sample and the results are averaged.

Utilizing a test of this nature, an appropriate hardness of a lotion for use in the present invention has a penetration of less than 30 mm in this test, for example in a range from about 5.0 to about 30 mm, more particularly from about 7.0 to about 25 mm, more particularly from about 12 to about 22 mm, and still more particularly from about 16 to about 22 mm.

Lotion Add-On

Lotion add-on was determined gravimetrically. A lotion treated web was cut off of the treated roll shortly after its manufacture and then die cut with a 10.1×10.1 cm die. Six stacks comprising 10 die cut sheets each were collected and then weighed on a scale to the nearest 0.01 g. The basis weight (gsm) of the treated sample was calculated by dividing the mass of the sample by its area (0.6194 $m^2$). An untreated tissue sample (control), run under the same process conditions, was sampled and its basis weight measured similarly. The treatment add-on (gsm) is the difference between the basis weights of the treated and untreated samples.

Tensile

Samples for tensile strength testing are prepared by cutting a 3 inches (76.2 mm)×5 inches (127 mm) long strip in either the machine direction (MD) or cross-machine direction (CD) orientation using a JDC Precision Sample Cutter (Thwing-Albert Instrument Company, Philadelphia, PA, Model No. JDC 3-10, Ser. No. 37333). The instrument used for measuring tensile strengths is an MTS Systems Sintech 11S, Serial No. 6233. The data acquisition software is MTS TestWorks™ for Windows Ver. 4 (MTS Systems Corp., Research Triangle Park, NC). The load cell is selected from either a 50 or 100 Newton maximum, depending on the strength of the sample being tested, such that the majority of peak load values fall between 10 and 90 percent of the load cell's full-scale value. The gauge length between jaws is 4±0.04 inches. The jaws are operated using pneumatic-action and are rubber coated. The minimum grip face width is 3 inches (76.2 mm), and the approximate height of a jaw is 0.5 inches (12.7 mm). The crosshead speed is 10±0.4 inches/min (254±1 mm/min), and the break sensitivity is set at 65 percent. The sample is placed in the jaws of the instrument, centered both vertically and horizontally. The test is then started and ends when the specimen breaks. The peak load is recorded as either the "MD tensile strength" or the "CD tensile strength" of the specimen depending on the sample being tested. At least six representative specimens are tested for each product, taken "as is," and the arithmetic average of all individual specimen tests is either the MD or CD tensile strength for the product.

Microscopy

The various surface planes and z-directional height differences may be measured using well-known microscopy techniques. For example, the cross-section image of a fibrous structure, web or tissue product, may be taken using a VHX-1000 Digital Microscope (Keyence Corporation of Osaka, Japan) equipped with VHX-H3M application software. Using the application software, a first line may be drawn approximately along the top surface plane of structure with the line tangent to two adjacent elevated elements. A second line is drawn approximately along the bottom surface plane of the structure with the line tangent to two adjacent land areas. With the two lines drawn, each corresponding to a surface plane of the structure, the application software can be instructed to calculate the distances between the planes.

EXAMPLES

A single-ply tissue product was produced using a through-air dried papermaking process commonly referred to as "uncreped through-air dried" ("UCTAD") and generally described in U.S. Pat. No. 5,607,551, the contents of which are incorporated herein in a manner consistent with the present disclosure.

Tissue basesheets were produced from a furnish comprising northern softwood kraft and *eucalyptus* kraft using a layered headbox fed by three stock chests such that the webs having three layers (two outer layers and a middle layer) were formed. The two outer layers comprised *eucalyptus* and the middle layer comprised softwood. The 3-layered structure had a furnish split of 33% EHWK/34% NBSK/33% EHWK, all on a weight percent basis.

The tissue web was formed on a Voith Fabrics TissueForm V forming fabric, vacuum dewatered to approximately 25 percent consistency and then subjected to rush transfer when transferred to the transfer fabric. The transfer fabric was the fabric described as "Fred" in U.S. Pat. No. 7,611,607 (commercially available from Voith Fabrics, Appleton, WI).

The web was then transferred to a through-air drying fabric. The through-air drying fabric was a silicone printed fabric described previously in co-pending PCT Appl. No. PCT/US2013/072220. Transfer to the through-drying fabric was done using vacuum levels of greater than 0.33 bars at the transfer. The web was then dried to approximately 98 percent solids before winding.

A hydrophobic lotion composition (Lotion Reference Code 1) was prepared by adding mineral oil (1547.9 g) to a stainless-steel beaker equipped with a hot plate and overhead stirrer. The mineral oil was heated with agitation to 65° C. Once heated, dimethicone (27.3 g) and isopropyl palmitate (77.6 g) were mixed with the mineral oil. Ceresin wax (470.9 g) was then mixed with agitation and heating to 65° C. After the wax was completely melted stearyl alcohol (470.9 g) was added, followed by the aloe extract (2.7 g) and vitamin E acetate (2.7 g). The composition was mixed for 5 minutes and then a UV optical brightening agent, Tinopal OB (2.6 g) and the visual colorant, Black Ink Exp R3989-123 (13.0 g) was added. The entire mixture was poured into a pan and allowed to cool overnight. The hardness of the resulting cake was measured as described above.

A hydrophilic lotion comprising propylene glycol and glycerin (Lotion Reference Code 2) was prepared by mixing propylene glycol (2576 g) and glycerin (1200 g) in a large beaker and the mixture was heated to 85° C. with good mixing but no air entrainment. Once at temperature and uniformly mixed, sodium stearate (200 g) was added and mixed until dissolved. A UV optical brightening agent, Tinopal OB (4 g), and a visual colorant, blue liquid dye (20 g), were added and mixed until uniform. The mixture was stirred and allowed to cool to 50° C., then poured into a pan and allowed to cool overnight. Total batch weight was 4000 g. The hardness of the resulting cake was measured as described above.

A hydrophobic lotion comprising polyethylene glycol (Lotion Reference Code 3) was prepared by mixing PEG 400 (3456 g) and PEG 8000 (520 g) in a large beaker and heating to 70° C. Once the PEGs were completely mixed, a UV optical brightening agent, Tinopal OB (4 g), and a visual colorant, blue liquid dye (20 g) were added and mixed until uniform. The mixture was allowed to cool slightly and poured into a pan and allowed to cool overnight. Total batch weight was 4000 g. The hardness of the resulting cake was measured as described above.

TABLE 1

| Lotion Reference Code | Penetration Hardness (mm) | Lotion Composition (wt %) |
|---|---|---|
| 1 | 16 | Mineral Oil (59.2%) |
|   |    | Ceresin Wax (18.0%) |
|   |    | Stearyl Alcohol (18.0%) |
|   |    | Isopropyl Palmitate (3.7%) |
|   |    | Dimethicone (1.3%) |
|   |    | Aloe Extract (0.13%) |
|   |    | Vitamin E Acetate (0.13%) |
| 2 | 15 | Propylene Glycol (37.4%) |
|   |    | Glycerin (60%) |
|   |    | Sodium Stearate (2%) |
| 3 | 14.5 | PEG 400 (86.4%) |
|   |    | PEG 8000 (13.0%) |

The basesheet was calendered-coated using an apparatus substantially similar to that illustrated in FIG. 6. The solid lotion was applied to a steel calender roll opposed to a conventional 40 P&J roll. In certain instances the steel calender roll was heated. The calender linear nip load ranged from about 40 to about 50 pli. The process conditions used to produce each of the inventive samples are set forth in Table 2, below.

TABLE 2

| Inventive Code | Lotion Reference Code | Lotion Thickness (mm) | Applicator Angle (°) | Lotion Feed Rate (mm/s) | Web Speed (mpm) | Calender Nip Load (pli) | Calender Temp. (° C.) | Lotion Add-On (gsm) |
|---|---|---|---|---|---|---|---|---|
| 287 | 1 | 16 | 0 | 0.4 | 152 | 50 | 21 | 3.1 |
| 292 | 1 | 16 | 0 | 0.5 | 152 | 50 | 63 | 3.3 |

TABLE 2-continued

| Inventive Code | Lotion Reference Code | Lotion Thickness (mm) | Applicator Angle (°) | Lotion Feed Rate (mm/s) | Web Speed (mpm) | Calender Nip Load (pli) | Calender Temp. (° C.) | Lotion Add-On (gsm) |
|---|---|---|---|---|---|---|---|---|
| 297 | 1 | 16 | 0 | 1.5 | 457 | 50 | 63 | 3.2 |
| 459 | 1 | 25 | 29.5 | 0.1 | 91 | 40 | 82 | 1.11 |
| 460 | 1 | 25 | 29.5 | 0.1 | 152 | 40 | 82 | 0.66 |
| 461 | 1 | 25 | 29.5 | 0.1 | 304 | 40 | 82 | 0.39 |
| 728 | 2 | 25 | 29.5 | 0.9 | 457 | 40 | 21 | 3.96 |
| 748 | 3 | 25 | 29.5 | 0.3 | 152 | 40 | 21 | 3.20 |

The lotion treated tissue web was converted to a finished rolled tissue product and subjected to physical testing. The results of the physical testing are summarized in Table 3, below.

TABLE 3

| Inventive Code | Basis Wt. (gsm) | Caliper (microns) | Sheet Bulk (cc/g) | GMT (g/3") | GM Slope (kg) | Stiffness Index |
|---|---|---|---|---|---|---|
| 287 | 43.3 | 696 | 16.1 | 796 | 5.33 | 6.7 |
| 292 | 41.7 | 691 | 16.6 | 760 | 4.93 | 6.5 |
| 297 | 42.3 | 864 | 20.4 | 752 | 4.35 | 5.8 |
| 459 | 40.6 | 749 | 18.5 | 793 | 4.82 | 6.1 |
| 460 | 40.0 | 752 | 18.8 | 780 | 4.70 | 6.0 |
| 461 | 39.6 | 765 | 19.3 | 763 | 4.51 | 5.9 |
| 728 | 43.7 | 798 | 18.3 | 586 | 4.17 | 7.1 |
| 748 | 43.3 | 724 | 19.3 | 778 | 5.15 | 6.6 |

Figure 7:
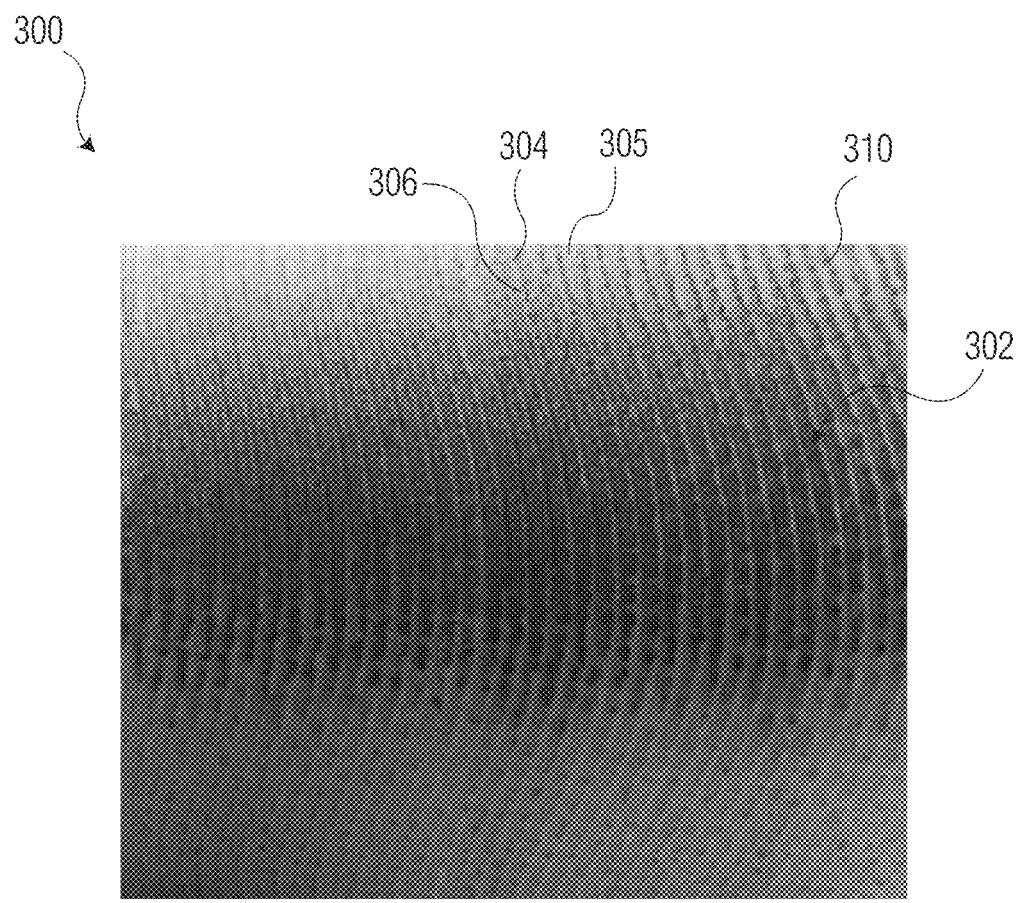
FIG. 7 is an image of a tissue product prepared as described in the example.

A photograph of the finished tissue product is shown in FIG. 7. The tissue product 300 has a first side 302 comprising a plurality of substantially similarly shaped continuous line elements 304 having upper surfaces 306 lying in a first surface plane. Between the line elements 304 are valleys 305 lying in a second surface plane below the first surface plane. A lotion 310 (dyed blue) is selectively disposed on the upper surface 306 of the continuous line elements 304.

While the invention has been described in detail in the foregoing description and example, those skilled in the art will appreciate that the present invention may be embodied in any one of several different embodiments including, for example:

In a first embodiment the present invention provides a treated fibrous structure comprising a textured fibrous web having a first side with a first surface lying in a first surface plane and a second surface lying in a second surface plane, the second surface plane lying below the first surface plane, and a lotion selectively disposed on the first surface.

In a second embodiment the present invention provides the web of the first embodiment wherein the lotion is applied as a solid having a penetration hardness from about 5.0 to about 30 mm.

In a third embodiment the present invention provides the web of the first or the second embodiments wherein the lotion is applied as a solid having a penetration hardness from about 5.0 to about 30 mm and comprises from about 30 to about 90 weight percent oil and from about 10 to about 40 weight percent wax.

In a fourth embodiment the present invention provides the web of any one of the first through the third embodiments wherein the lotion is applied as a solid having a penetration hardness from about 10 to about 20 mm and comprises from about 30 to about 90 weight percent oil selected from the group consisting of mineral oil, animal oil, plant oil and silicone oil, from about 10 to about 40 weight percent wax selected from the group consisting of natural wax, petroleum wax, silicone wax and synthetic wax and from about 15 to about 25 weight percent fatty alcohol selected from the group consisting of cetyl alcohol, stearyl alcohol, behenyl alcohol and dodecyl alcohol.

In a fifth embodiment the present invention provides the web of any one of the first through the fourth embodiments wherein the product has a caliper and the z-directional height difference between the first and the second surface planes is at least about 10 percent of the caliper.

In a sixth embodiment the present invention provides the web of any one of the first through the fifth embodiments wherein the product has a caliper and the z-directional height difference between the between the first and the second surface planes is at least 100 μm, such as from about 100 to 200 μm.

In a seventh embodiment the present invention provides the web of any one of the first through the sixth embodiments wherein the first surface plane is formed by a design element, which in certain embodiments may comprise a continuous line element or a discrete line element.

In an eighth embodiment the present invention provides the web of any one of the first through the seventh embodiments wherein the product has a basis weight greater than about 10, such as from about 10 to about 60 and more preferably from about 30 to about 60 grams per square meter (gsm), and a geometric mean tensile (GMT) greater than about 500 g/3", such as from about 500 to about 4,000 g/3" and more preferably from about 750 to about 3,500 g/3".

In a ninth embodiment the present invention provides the web of any one of the first through the eight embodiments wherein the product comprises a single-ply through-air dried tissue web.

In a tenth embodiment the present invention provides the web of any one of the first through the ninth embodiments wherein the product has a caliper greater than about 300 μm and a sheet bulk greater than about 5 cc/g. In particularly preferred embodiments the product has a caliper greater than about 400 μm and a sheet bulk greater than about 10 cc/g.

In an eleventh embodiment the present invention provides the web of any one of the first through the tenth embodiments wherein the product has a GMT ranging from about 700 to about 1,200 g/3".

In a twelfth embodiment the present invention provides the web of any one of the first through the eleventh embodiments wherein the product has a GM Slope ranging from 4.0 to about 7.0 kg.

In a thirteenth embodiment the present invention provides the web of any one of the first through the twelfth embodiments wherein the product has a Stiffness Index ranging from about 4.0 to about 8.0.

We claim:

1. A method of manufacturing a lotion treated web comprising the steps of:

a. providing a first lotion composition having a penetration hardness ranging from about 5 to about 30 mm;
b. providing nip between a steel calender roll and a polymer coated calender roll;
c. applying the first lotion to the steel calender roll;
d. conveying a textured fibrous web having an upper most surface through the nip whereby one outwardly facing surface of the web is contacted by the steel calender roll resulting in a transfer of the first lotion to the surface of the textured fibrous web.

2. The method of claim 1 wherein the steel calender roll is heated and has a surface temperature ranging from about 70° C. to about 100° C.

3. The method of claim 1 wherein the steel calender roll is heated and has a surface temperature ranging from about 70° C. to about 90° C.

4. The method of claim 1 wherein the lotion comprises from about 30 weight percent (wt %) to about 90 wt % oil and from about 10 wt % to about 40 wt % wax.

5. The method of claim 1 wherein the lotion has a penetration hardness from about 10 to about 20 mm and comprises at least one oil selected from the group consisting of mineral oil, animal oil, plant oil and silicone oil, at least one wax selected from the group consisting of natural wax, petroleum wax, silicone wax and synthetic wax and at least one fatty alcohol selected from the group consisting of cetyl alcohol, stearyl alcohol, behenyl alcohol and dodecyl alcohol.

6. The method of claim 5 wherein the lotion comprises from about 30 to about 90 weight percent oil, from about 10 wt % to about 40 wt % wax and from about 15 wt % to about 25 wt % fatty alcohol.

7. The method of claim 1 wherein the lotion comprises a high molecular weight polyethylene glycol or propylene glycol.

8. The method of claim 1 wherein the web has a first side to be contacted by a user in-use, the first side having an uppermost surface lying in a first surface plane and a second surface lying in a second surface plane, the second surface plane lying below the first surface plane, and a lotion selectively disposed on the uppermost surface.

9. The method of claim 1 wherein the web has a web caliper and the web caliper is reduced after being conveyed through the nip.

10. The method of claim 1 wherein the lotion is selectively disposed on the uppermost surface in an amount ranging from about 0.20 to about 3.0 grams per square meter of textured fibrous web.

11. The method of claim 1 wherein the web has a total surface area and the lotion is transferred to about 70 percent to about 95 percent of the total surface area of the web.

12. The method of claim 1 wherein the step of applying the lotion to the steel calender roll comprises urging the first lotion against the steel calender roll at a feed rate ranging from about 0.05 to about 0.2 mm per second.

13. The method of claim 1 wherein the web is conveyed through the nip at a speed ranging from about 15 to about 300 meters per minute (mpm).

14. The method of claim 1 further comprising the steps of providing a second lotion having a penetration hardness ranging from about 5 to about 30 mm and applying the second solid lotion to the steel calender roll, wherein the first and the second solid lotions are different.

* * * * *